United States Patent [19]

Louderback

[11] 4,189,401
[45] Feb. 19, 1980

[54] METHOD OF STORING A BIOLOGICAL REFERENCE CONTROL STANDARD AND BIOLOGICAL REFERENCE CONTROL STANDARD OBTAINED THEREBY

[75] Inventor: Allan L. Louderback, Temple City, Calif.

[73] Assignee: Beckman Instruments, Inc., Fullerton, Calif.

[21] Appl. No.: 925,482

[22] Filed: Jul. 17, 1978

[51] Int. Cl.² .................... C09K 3/00; G01N 33/16
[52] U.S. Cl. .............................. 252/408; 23/230 B; 435/4; 356/39; 356/243; 424/3; 424/95; 424/101
[58] Field of Search ............... 23/230 B; 252/408; 424/2, 3, 101, 95; 356/39, 243; 195/103.5 R

[56] References Cited

U.S. PATENT DOCUMENTS

| 3,876,375 | 4/1975 | Maurukas | 252/408 |
| 4,121,905 | 10/1978 | Maurukas | 252/408 |

OTHER PUBLICATIONS

C.A., vol. 84, p. 314, 133466n (1976).
C.A., vol. 83, p. 524, 6047b & 6049h (1975).
C.A., vol. 82, p. 262, 70864b (1975).
C.A., vol. 81, p. 278, 75600b (1974).
C.A., vol. 80, p. 230, 93682p (1974).
C.A., vol. 80, p. 289, 131126v & 131127w (1974).

*Primary Examiner*—Benjamin R. Padgett
*Assistant Examiner*—T. S. Gron
*Attorney, Agent, or Firm*—R. J. Steinmeyer; Robert S. Frieman

[57] ABSTRACT

An improved method of storing and shipping a blood serum reference composition comprising in its non-biological component from about 40 to about 85 weight percent water, from about 15 to about 60 weight percent of at least one alkylene polyol having from 2-5 carbon atoms, the remainder being chiefly at least one natural biological material selected from a group consisting of blood serum, enzyme, metabolites, electrolytes, and hormones. The improvement comprises storing and/or shipping the composition at a temperature below the freezing point thereof.

10 Claims, No Drawings

METHOD OF STORING A BIOLOGICAL REFERENCE CONTROL STANDARD AND BIOLOGICAL REFERENCE CONTROL STANDARD OBTAINED THEREBY

BACKGROUND OF THE INVENTION

1. Field of the Invention

This invention relates to a method of storing and shipping a blood serum reference composition as well as to a blood serum reference composition obtained thereby.

2. Description of the Prior Art

U.S. Pat. No. 3,876,375 (hereinafter referred to as Maurukas patent) is incorporated herein in toto by reference. The Maurukas patent discloses a stable, blood serum biological reference composition for use in analysis of biologically similar unknowns. Depending upon its precise constitution, the Maurukas composition has a freezing temperature at from about $-20°$ C. to about $-30°$ C. and is capable of extended storage in the liquid state. The Maurakas composition comprises, in its non-biological component, from about 60 to about 80 weight percent water and from about 20 to about 40 weight percent of at least one alkylene polyol having from 2 to 5 carbon atoms. The remainder of the composition is chiefly at least one natural biological material selected from a group consisting of blood serum, enzyme, metabolites, electrolytes, and hormones.

As noted in the Maurukas patent, the widely accepted procedure, prior to Maurukas' invention, was to preserve labile biologicals containing water by rapidly freezing them and storing them in the frozen state at low temperatures until ready for use. One problem pointed out by the Maurukas patent as being inherent in this prior art procedure is that freezing does, in some cases, produce insoluble turbidity when the biological material is brought back to the liquid state, and especially when it is brought to room temperature.

It is also well known to those skilled in the art that when serum is frozen to about $-20°$ C., there is some degradation of the proteins and enzymes and some loss of gases as they are squeezed out of the matrix during the freezing process. Repeated freezing and thawing of the serum will also dissociate isoenzymes of LDH and CPK. Therefore, when such serum is assayed for LDH and CPK isoenzymes, one obtains inaccurate values as to the relative percentage of each of these isoenzymes in the serum. The repeated freezing and thawing effect on serum proteins in general will cause a change in antigenicity with a decrease value for antigen-antibody reactions. This decrease in value for antigen-antibody reactions results in lower concentration values for the antigen being assayed.

To overcome the above problems inherent in freeze-drying serum as well as in storing serum at a temperature below the freezing point thereof, Maurukas removed from about 20 to about 40 weight percent water from frozen serum and added to the concentrated serum one or more alkylene polyols in an amount equal to the amount of water removed therefrom. Maurukas thereby obtained a biological composition which could be stored as a liquid at a temperature of from about $-30°$ C. to about room temperature.

SUMMARY OF THE INVENTION

It has been discovered that by freezing the Maurukas type blood serum reference composition below the freezing point thereof, one is able to enhance the shelf life thereof without incurring the usual denaturalization process observed when biological compositions are subjected to one or more freeze-thaw routines. Furthermore, after freezing the Maurukas type blood serum composition below the freezing point thereof, the frozen composition acts as its own heat sink during shipment. This capability further insures maximum stability during shipment by preventing heat denaturization.

DESCRIPTION OF THE PREFERRED EMBODIMENTS

The improved method of storing a blood serum reference composition of the Maurukas type entails storing said composition at a temperature below the freezing point thereof. Preferably, the composition is stored at a temperature below the freezing point thereof and above the freezing point of carbon dioxide. More preferably, the composition is stored at a temperature of from about $-25°$ to about $-75°$, and more preferably, from about $-40°$ to about $-50°$ C.

In the instant invention, it is also possible, but not preferred, to store a blood serum reference composition which comprises in its non-biological component from about 40 to about 85 weight percent water and from about 15 to about 60 weight percent of at least one alkylene polyol having from 2 to 5 carbon atoms, the remainder being, as in the case of Maurukas' composition, chiefly at least one natural biological material selected from a group consisting of blood serum, enzyme metabolites, electrolytes, and hormones.

The following examples are provided for the purpose of further illustration and are not intended to be limitations on the disclosed invention.

EXAMPLE 1

Approximately 5 milliliters each of serum A and serum B, having initial compositions as set forth in Table I, were placed in one plastic and one glass vial. The serums were fast frozen by placing the vials in acetone and dry ice (about $-76°$ C.) for about one minute and swirling. The vials were then removed to room temperature (about 25° C.) with swirling in a cup of water for about one minute. This procedure was repeated 50 times. The samples were then assayed on a Technicon SMA-12/60 TM brand and SMA-6/60 TM analyzer. The test results are set forth in Table I.

Table I

| | A | | B | |
|---|---|---|---|---|
| Constituent | Initial Values | Values After 50 Freeze/Thaw Routines | Initial Values | Values After 50 Freeze/Thaw Routines |
| Calcium | 10.5 | 10.5 | 10.0 | 10.2 |
| Phosphorus | 5.8 | 5.6 | 5.6 | 5.5 |
| Glucose | 256 | 255 | 253 | 258 |
| BUN | 47 | 47 | 47 | 48 |
| Uric Acid | 9.6 | 9.5 | 9.6 | 9.6 |
| Cholesterol | 140 | 144 | 141 | 143 |
| Total Protein | 5.5 | 5.5 | 5.4 | 5.6 |
| Albumin | 2.9 | 3.2 | 2.8 | 3.2 |
| T. Bilirubin | 2.8 | 2.9 | 4.4 | 4.5 |
| Alk. Phos. | 173 | 158 | 234 | 235 |
| LDH | 563 | 563 | 592 | 591 |
| SGOT | 65 | 60 | 73 | 76 |
| Sodium | 180 | 179 | 181 | 181 |
| Potassium | 6.9 | 6.7 | 6.7 | 6.9 |
| Chloride | 98 | 98 | 98 | 99 |
| $CO_2$ | 10 | 10 | 18 | 20 |
| Creatinine | 4.4 | 4.5 | 5.2 | 4.5 |

Table I-continued

| | A | | B | |
|---|---|---|---|---|
| Constituent | Initial Values | Values After 50 Freeze/Thaw Routines | Initial Values | Values After 50 Freeze/Thaw Routines |
| SGPT | 70 | 87 | 74 | 91 |

The data set forth in Table I clearly shows the unobvious phenomena exhibited by the process and composition of the instant invention. Namely, it is quite surprizing in view of the prior art to be able to repeatedly freeze and thaw a blood serum reference composition without detrimentally affecting its biological constituents.

It is also surprising that the shelf-life of the Maurukas type composition is longer when the composition is stored in a frozen state than when stored in the liquid state. This phenomena is unobvious because one skilled in the art would think that in the frozen state the composition would slowly lyophilize, i.e., out gas water. However, such lyophilization was not observed after extended storage of the composition in the frozen state.

Those skilled in the art also known that proteins dissolved in polyethylene glycol are precipitated when the polyethylene glycol is frozen. Therefore, it is unobvious to find that alkylene polyols containing from 2 to 5 carbon atoms do not precipitate out proteins dissolved therein when these alkylene polyols are frozen.

Based on this disclosure, many other modifications and ramifications will naturally suggest themselves to those skilled in the art. These are intended to be comprehended as within the scope of this invention.

The embodiments of the invention in which an exclusive property or privilege is claimed are defined as follows:

1. An improved method of storing a blood serum reference composition for subsequent use in analysis of biologically similar unknowns, said composition comprising in its non-biological component from about 40 to about 85 weight percent water, from about 15 to about 60 weight percent of at least one alkylene polyol having from 2 to 5 carbon atoms, the remainder being chiefly at least one labile natural biological material selected from a group consisting of blood serum, enzyme, metabolites, electrolytes, and hormones, wherein the improvement comprises lowering the temperature of said composition to below the freezing point thereof and storing said composition in a frozen state.

2. The method of claim 1 wherein said non-biological component comprises from about 60 to about 80 weight percent water and from about 20 to about 40 weight percent of said alkylene polyol and wherein said composition is stored at a temperature below the freezing point thereof and above the freezing point of carbon dioxide.

3. The method of claim 2 wherein said composition is stored at a temperature of from about $-25°$ to about $-75°$ C.

4. The method of claim 3 wherein said composition is stored at a temperature of from about $-40°$ to about $-50°$ C.

5. The method of claim 1 wherein said non-biological component comprises from about 60 to about 80 weight percent water and from about 20 to about 40 weight percent of said alkylene polyol and wherein said composition is stored at a temperature below $-25°$ C.

6. A frozen blood serum reference composition for use in analysis of biologically similar unknowns upon thawing, said composition comprising in its non-biological component from about 40 to about 85 weight percent water, from about 15 to about 60 weight percent of at least one alkylene polyol having from 2 to 5 carbon atoms, the remainder being chiefly at least one labile natural biological material selected from a group consisting of blood serum, enzymes, metabolites, electrolytes, and hormones.

7. The composition of claim 6 wherein said non-biological component comprises from about 60 to about 80 weight percent water and from about 20 to about 40 weight percent of said alkylene polyol and wherein said composition is frozen at a temperature below its freezing point and above the freezing point of carbon dioxide.

8. The composition of claim 7 wherein said composition is frozen at a temperature of from about $-25°$ to about $-75°$ C.

9. The composition of claim 8 wherein said composition is frozen at a temperature of from about $-40°$ to about $-50°$ C.

10. The composition of claim 6 wherein said nonbiological component comprises from about 60 to about 80 weight percent water and from about 20 to about 40 weight percent of said alkylene polyol and wherein said composition is frozen at a temperature below $-25°$ C.

* * * * *